US011821741B2

(12) United States Patent
Petersen et al.

(10) Patent No.: US 11,821,741 B2
(45) Date of Patent: Nov. 21, 2023

(54) STRESS MAP AND VEHICLE NAVIGATION ROUTE

(71) Applicant: LP-RESEARCH INC., Tokyo (JP)

(72) Inventors: Klaus Petersen, Tokyo (JP); Zhouhua Lin, Tokyo (JP); Huei Ee Yap, Tokyo (JP); Tobias Schlüter, Tokyo (JP)

(73) Assignee: LP-Research Inc., Tokyo (JP)

( * ) Notice: Subject to any disclaimer, the term of this patent is extended or adjusted under 35 U.S.C. 154(b) by 971 days.

(21) Appl. No.: 15/955,294

(22) Filed: Apr. 17, 2018

(65) Prior Publication Data
US 2019/0316922 A1 Oct. 17, 2019

(51) Int. Cl.
| | |
|---|---|
| G01C 21/34 | (2006.01) |
| G01C 21/36 | (2006.01) |
| A61B 5/01 | (2006.01) |
| A61B 5/024 | (2006.01) |
| A61B 5/16 | (2006.01) |
| A61B 5/18 | (2006.01) |
| A61B 5/00 | (2006.01) |
| A61B 7/00 | (2006.01) |

(52) U.S. Cl.
CPC ............ *G01C 21/3461* (2013.01); *A61B 5/01* (2013.01); *A61B 5/02416* (2013.01); *A61B 5/165* (2013.01); *A61B 5/18* (2013.01); *A61B 5/6893* (2013.01); *A61B 7/00* (2013.01); *G01C 21/3415* (2013.01); *G01C 21/3484* (2013.01); *G01C 21/3492* (2013.01); *G01C 21/3617* (2013.01); *G01C 21/3623* (2013.01); *G01C 21/3667* (2013.01); *A61B 2562/0247* (2013.01)

(58) Field of Classification Search
CPC ....... A61B 5/01; A61B 5/02416; A61B 5/165; A61B 5/18; A61B 5/6893; A61B 7/00; G01C 21/3415; G01C 21/3484; G01C 21/3492; G01C 21/3617; G01C 21/3623; G01C 21/3667

USPC ........................................................ 701/423
See application file for complete search history.

(56) References Cited

U.S. PATENT DOCUMENTS 6,599,243 B2   7/2003   Woltermann et al.
6,946,966 B2   9/2005   Koenig
(Continued)

FOREIGN PATENT DOCUMENTS

EP   1291226 A2      3/2003
EP   1291226 A2 *  12/2003
(Continued)

OTHER PUBLICATIONS

Rogers, Seth, et al., "A Route Advice Agent that Models Driver Preferences," Proceeding of the AAAI Symposium, Stanford, California, 1999.

Singh, Rajiv Ranjan, et al., "A comparative evaluation of neural network classifiers for stress level analysis of automotive drivers using physiological signals," Biomedical Signal Processing and Control 8, pp. 740-754, 2013.

(Continued)

*Primary Examiner* — Maceeh Anwari
(74) *Attorney, Agent, or Firm* — Erise IP, P.A.

(57) ABSTRACT

System, method, and media for providing navigation of an affective vehicle environment to an occupant (such as a driver) of a vehicle. Sensors in and on the vehicles in the affective environment may detect characteristics of the occupants of the vehicle and stress levels may be assigned to the occupants. The navigation may be based at least in part on the location and destination of the vehicles in the affective environment and the stress levels of the occupants of the vehicles.

20 Claims, 5 Drawing Sheets

(56) References Cited

U.S. PATENT DOCUMENTS

| | | | |
|---|---|---|---|
| 7,821,382 | B2 | 10/2010 | Kameyama |
| 8,874,301 | B1 | 10/2014 | Monoharprasad et al. |
| 2006/0283652 | A1 | 12/2006 | Yanai et al. |
| 2007/0066916 | A1 | 3/2007 | Lemos |
| 2009/0160631 | A1 | 6/2009 | Galley |
| 2009/0209829 | A1 | 8/2009 | Yanagidaira et al. |
| 2015/0053066 | A1 | 2/2015 | Hampifoli |
| 2018/0340785 | A1* | 11/2018 | Upadhyay .......... G01C 21/3469 |

FOREIGN PATENT DOCUMENTS

| | | | |
|---|---|---|---|
| JP | 2014-146289 A | | 8/2014 |
| JP | 2015-35081 A | | 2/2015 |
| JP | 2015035081 A | * | 2/2015 |
| JP | 2015-191256 A | | 11/2015 |
| JP | 2015191256 A | * | 11/2015 |
| WO | WO2015134376 A1 | * | 3/2015 |
| WO | 2015134376 A1 | | 9/2015 |
| WO | 2017/051478 A1 | | 3/2017 |

OTHER PUBLICATIONS

Kumar, Mohit, et al., "Fuzzy Evaluation of Heart Rate Signals for Mental Stress Assessment," IEEE Transactions on Fuzzy System, vol. 15, No. 5, Oct. 2007.

Rigas, George, et al., "Real-Time Driver's Stress Event Detection," IEEE Transactions on Intelligent Transportation Systems, vol. 13, No. 1, Mar. 2012.

Sierra, Alberto de Santos, et. al., "A Stress-Detection System Based on Physiological Signals and Fuzzy Logic," IEEE Transactions On Industial Electronics, vol. 58, No. 10, Oct. 20011.

Coughlin, Joseph F., et al. "Monitoring, Managing, and Motivating Driver Safety and Well-being," Purvasive Computing, Jul.-Sep. 2011.

Fanci, Near-Markeet Innovation Action Automotive Use Cases,— http://www.fanci-project.eu/, Printed Apr. 17, 2018, copyright 2018.

NVISO, Insights For Market Researchers, http://www.nviso.ch/, printed Sep. 27, 2017, copyright 2016.

PCT Patent Application PCT/IB2018/052719 International Search Report and Written Opinion dated Jun. 7, 2018, 9 pages.

* cited by examiner

STRESS MAP AND VEHICLE NAVIGATION ROUTE

BACKGROUND

1. Field

Embodiments of the invention generally relate to vehicular safety and, more particularly, to techniques for reducing unsafe stress levels in vehicle operators through the use of detecting the stress levels of drivers, creating a map of stress zones indicative of drivers with elevated stress levels, and determining driving routes for the drivers.

2. Related Art

Reckless operation of motor vehicles by high stress drivers is a major cause of traffic accidents just like alcohol, drug, and cell phone use. Stress may be quantified into levels of experienced by the driver of the vehicles. The ability to determine and foresee what nearby drivers are doing and might do is critical to recognizing and reacting to road hazards such as debris and abrupt slowing of the traffic ahead. Other dangerous maneuvers may include sudden changes in traffic lanes and driving on the freeway shoulder or center divider. The emotional states that cause these hazardous conditions may be induced by the driver's stress level. A heightened stress level may cause a person to act erratically thus resulting in the actions described above.

The driver's stress level may be affected by influences in and out of the driver's control. For example, the driver may be late because the driver forgot to set an alarm. This may heighten the stress of the individual and may be prevented. An accident on the road ahead of the driver may cause the traffic to slow and the driver may be even later. This may be out of the driver's control. Any form of stress may also negatively affect a person's health. The stress level of the driver may be compounded by the traffic on the road. What is needed is a system that may reduce the stress level of the drivers by avoiding other drivers that have high stress or suggesting driving routes that avoid areas that may increase stress.

SUMMARY

Embodiments of the invention address the above-described by providing for a system which uses machine learning algorithms to determine a driver's stress level and provide a stress map indicative of drivers' stress levels and provide a driving route to a driver based on the stress map.

In particular, in a first embodiment, the invention includes a system for generating a map of an affective traffic environment based at least in part on a location and a destination of a first vehicle, comprising a first sensor configured to collect a first set of data associated with a driver of the first vehicle, a second sensor configured to collect a second set of data associated with a driver of a second vehicle, a processor, one or more non-transitory computer storage media storing a first driver profile based at least in part on the first set of data, a second driver profile based at least in part on the second set of data, the destination and the location of the first vehicle, computer-executable instructions that, when executed by the processor, perform a method of generating a map of an affective traffic environment based at least in part on the destination and the location of the first vehicle, comprising the steps of calculating a first stress level from the first driver profile, calculating a second stress level from the second driver profile, calculating a stress zone based at least in part on the second stress level and a location of the second vehicle, calculating a driving route for the first vehicle based at least in part on the stress zone, and communicating with a second processor configured to display the map of the affective driving environment to the first driver, wherein the map includes the driving route and the stress zone.

In a second embodiment, the invention includes a method of generating a map of an affective traffic environment based at least in part on a destination and a location of a first vehicle, comprising the steps of collecting via at least one sensor a first set of data associated with the driver of the first vehicle, collecting via at least one second sensor a second set of data associated with the driver of a second vehicle, determining a first stress level from the first set of data, determining a second stress level from the second set of data, generating the map of the affective traffic environment, generating a stress zone from at least the second stress level and a location of the second vehicle, generating a recommended driving route for the first vehicle based at least in part on the stress zone, and displaying the map of the affective traffic environment of the first vehicle, stress zone, and recommended driving route to the driver of the first vehicle.

In a third embodiment, the invention includes one or more computer storage media storing computer-executable instructions that, when executed by a processor, perform a method of generating a map of an affective traffic environment based at least in part on a destination and a location of a vehicle, the method comprising the steps of sensing a stress level of an occupant of the vehicle, generating the map of the affective traffic environment of the vehicle based at least in part on a location of the vehicle, displaying the map of the affective traffic environment to the occupant of the vehicle, and recommending a driving route to the occupant of the vehicle via the map of the affective traffic environment, wherein the driving route is based at least in part on the stress level of the occupant of the vehicle, location of the vehicle, destination of the vehicle, and information associated with the other traffic in the affective traffic environment.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 4A:
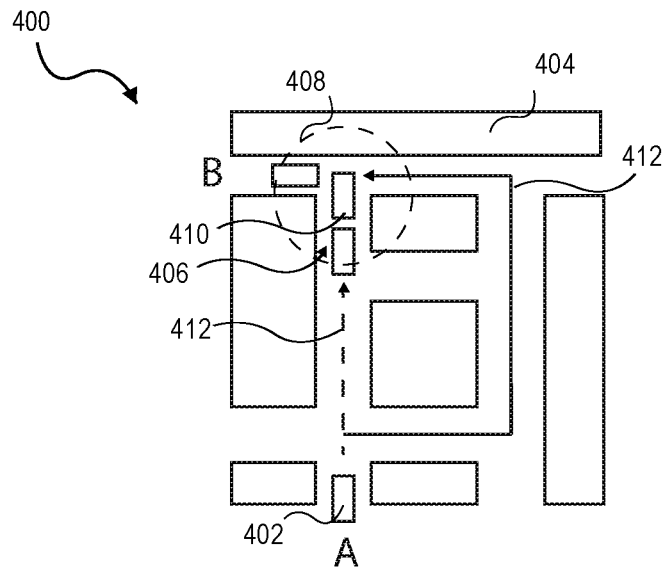
Figure 4B:
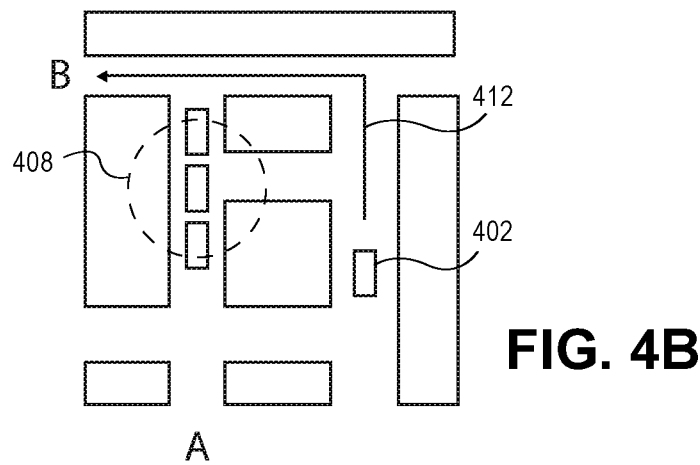
Figure 4C:
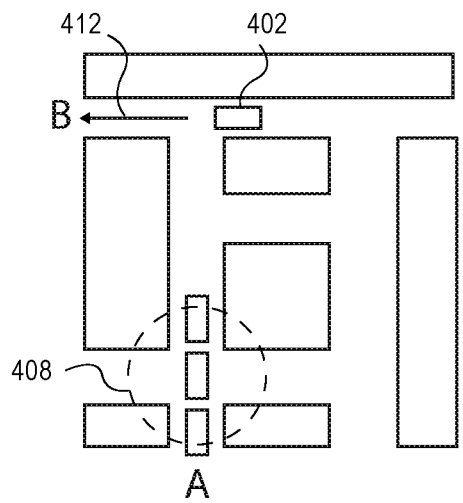
Figure 5:
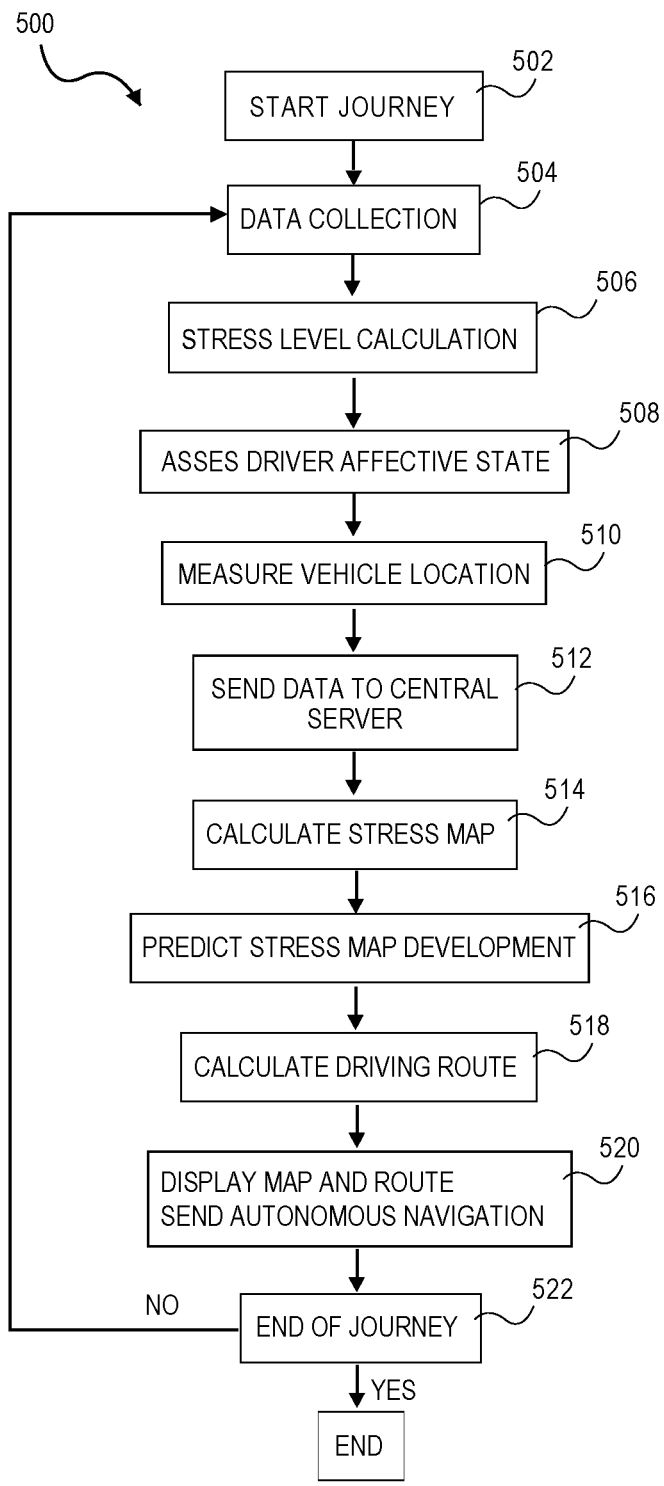

FIGS. 4A-C depict an exemplary stress map, stress zones, and driving route in some embodiments of the invention; and FIG. 5 depicts a flow chart representing an exemplary method associated with embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

Driving in a heightened stress state may be mitigated by routing a driver through low-stress areas. At a high level, embodiments of the invention relate to detecting the location and the stress levels of drivers in an affective traffic environment. Broadly speaking, the affective traffic environment describes the affect (i.e., the mood, emotional state, or stress level) of the drivers and/or other vehicle occupants in a particular area. The affective traffic environment may be determined by the location and the destination of a vehicle and may be any traffic, roadways, man-made objects, or natural objects that the vehicle may come in contact with over the course of travel. The stress level of the occupant of the vehicle as well as the stress levels of the occupants of other vehicles in the affective traffic environment may be measured through a plurality of sensors on the vehicles. The stress levels may be calculated and stored over time. The system may then generate a map of the affective traffic environment including any man-made and natural landmarks, and generate a navigation route, or driving route, through the affective traffic environment based at least in part on the location of the vehicle, destination of the vehicle, stress levels of the occupants of the vehicles, and the locations of the vehicles.

The subject matter of embodiments of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be obvious to one skilled in the art, and are intended to be captured within the scope of the claimed invention. Terms should not be interpreted as implying any particular ordering of various steps described unless the order of individual steps is explicitly described.

The following detailed description of embodiments of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of embodiments of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments, but is not necessarily included. Thus, the technology can include a variety of combinations and/or integrations of the embodiments described herein.

Figure 1:
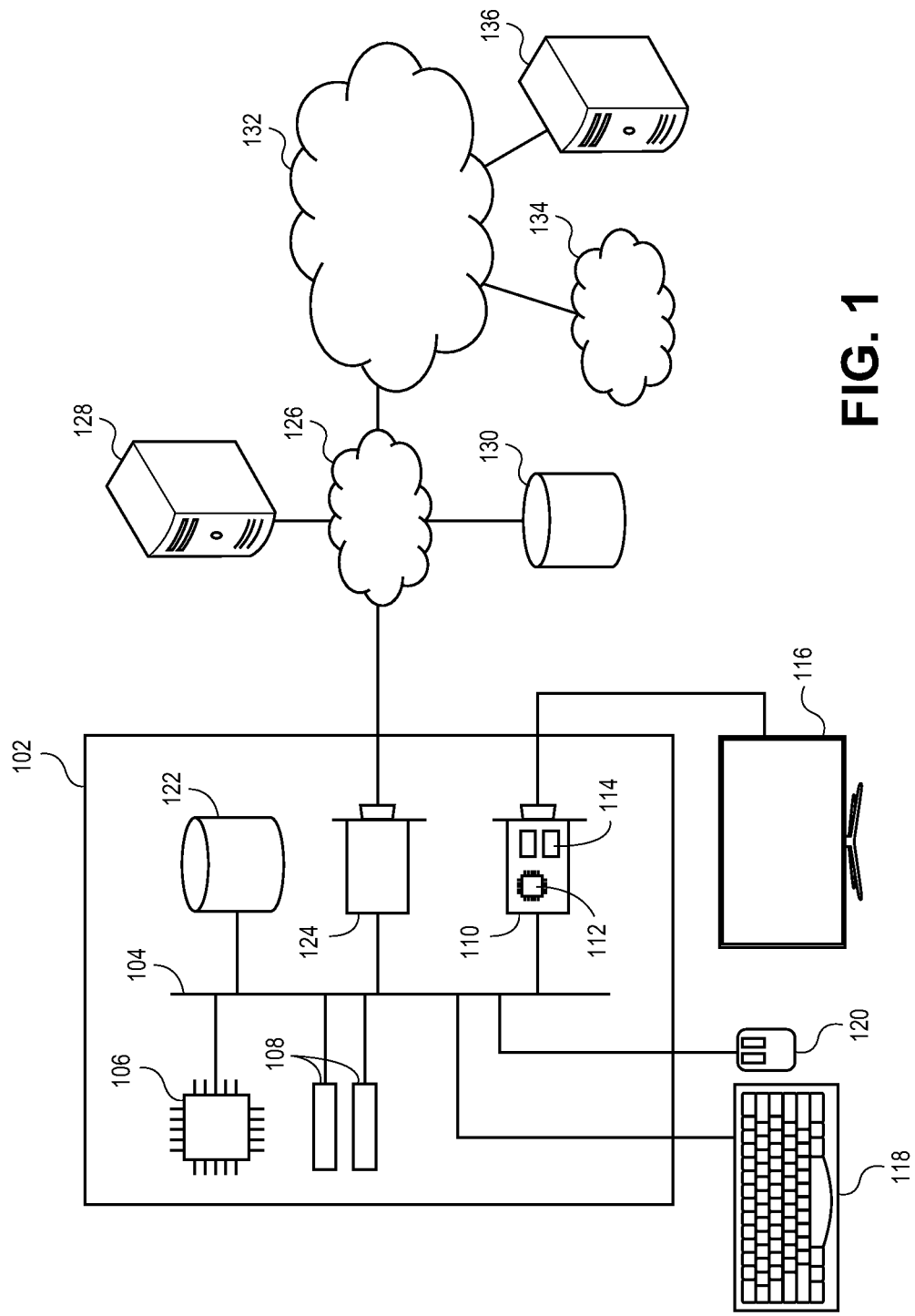
FIG. 1 depicts an exemplary hardware platform for certain embodiments of the invention.

Turning first to FIG. 1, an exemplary hardware platform for certain embodiments of the invention is depicted. Computer 102 can be a desktop computer, a laptop computer, a server computer, a mobile device such as a smartphone or tablet, or any other form factor of general- or special-purpose computing device. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 104 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-useable instructions, data structures, program modules, and other data representations.

Finally, network interface card (NIC) 124 is also attached to system bus 104 and allows computer 102 to communicate over a network such as network 126. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

Figure 2:
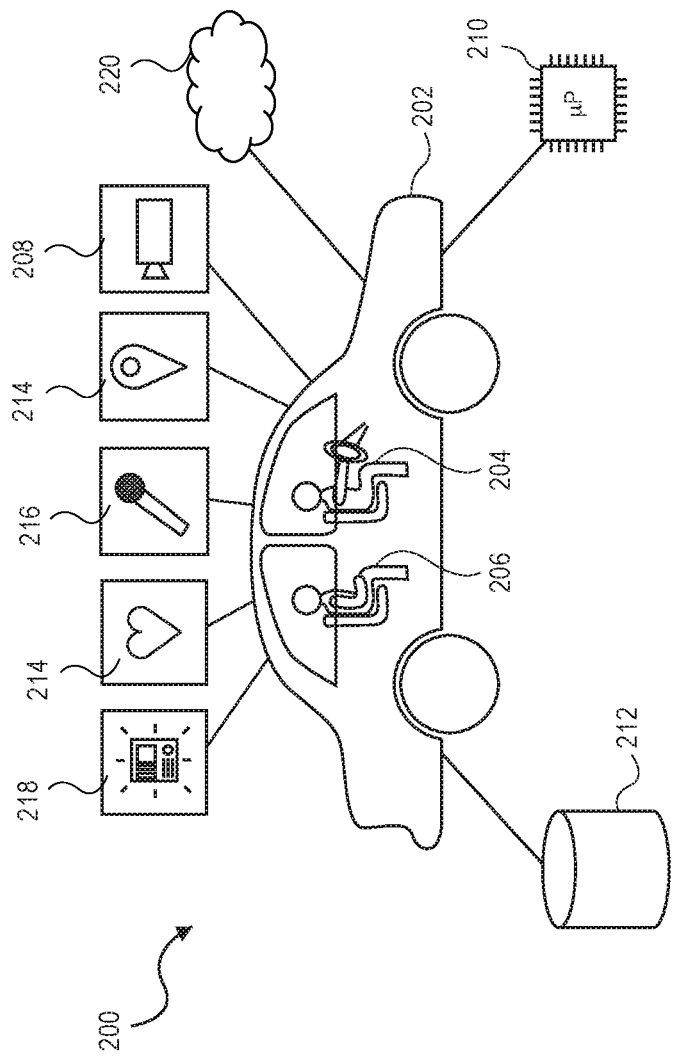
FIG. 2 depicts a system suitable for employing the embodiments of the invention.

Turning now to FIG. 2, an exemplary environment suitable for deploying certain embodiments of the invention is depicted and referred to generally by reference numeral 200. Vehicle 202 is one example of a platform suitable for embodiments of the invention. For example, vehicle 202 may be a car, truck, sport utility vehicle, or any other form of transportation. In some embodiments, vehicle 202 may instead be an airplane, train, boat, or other method of transportation. Broadly speaking, any form of public or private conveyance is contemplated as being within the scope of the invention. Vehicle 202 may be a conventional (driver-operated) vehicle, an autonomous (self-driving) vehicle, or a hybrid of the two (for example, a partially autonomous vehicle requiring a driver presence but only limited activity or supervision).

Vehicle 202 has one or more occupants such as driver 204 and passenger 206. In some embodiments, vehicle 202 is autonomous and has no driver 204. In some embodiments, vehicle 202 has a plurality of passengers 206. In other embodiments, vehicle 202 has no passengers 206. Broadly speaking, embodiments of the invention can be used whenever vehicle 202 has any number of occupants of any type, including zero.

Also present in vehicle 202 are one or more cameras 208 positioned to capture facial imagery of the driver 204 and/or the passenger 206. In some embodiments, cameras 208 capture visible-spectrum light. In other embodiments, cameras 208 capture infrared light instead of (or in addition to) visible light. In some embodiments, cameras 208 may be equipped with a visible or infrared light source (for example, one or more light-emitting diodes of the appropriate frequency or frequencies). In some embodiments, cameras 208 are fixedly oriented; in other embodiments, cameras 208 can be automatically or manually re-aimed. For example, cameras 208 may be mounted via pan/tilt/zoom mounts so as to continuously capture imagery of driver 204 and/or passenger 206 regardless of their movements. In some embodiments, only a single camera 208 is present, but it is mounted via a pan/tilt/zoom mount so as to selectively capture imagery of different occupants. In some embodiments, additional sensors are also present. For example, cameras 208 may be supplemented by a heart-rate sensor integrated into a steering wheel of vehicle 202. Other sensors (e.g., accelerometers for detecting occupant motion) for determining the stress level or behavior of the occupants of vehicle 202 are also contemplated as being within the scope of the invention.

Cameras 208 are communicatively coupled to processor 210 and/or data store 212. Processor 210 may further be communicatively coupled to any of the components described above with respect to FIG. 1. For example, a touchscreen display for processor 201 may be integrated into the dashboard of vehicle 202. In some embodiments, processor 210 may be connected to the CAN (Controller Area Network) or VAN (Vehicle Area Network) bus for vehicle 202, and can obtain driving performance data therefrom to assist in stress level classification for driver 204. In some embodiments, cameras 208 transmit imagery to processor 210. In other embodiments, cameras 208 store imagery in data store 212 for later processing by processor 210. In some embodiments, the data and/or stress level information may be sent to a central server for storage and processing. Data store 212 may also store configuration data for the system and one or more occupant stress profiles or any sensor data, as discussed in greater detail below.

Continuing with the exemplary embodiment depicted in FIG. 2, the vehicle 202 may be configured with multiple sensors including the camera 208 for detecting the emotional state and determining a stress level of the driver 204. For example, a blood pressure monitor 214, microphone 216, galvanometer (not shown), or any other general sensor 218 or device that may be used to monitor any physical condition of the driver 204 may be used. The system may detect many factors, or physical characteristics of the driver 204 related to determining a stress level of the driver 204 such as heart rate, facial expressions, voice pitch, breath rate, pupil dilation, muscle tension, skin conductivity, movement, or any other condition of the driver that may be useful in determining an emotional state or stress level. The general sensor 218 may be configured to detect any of the above-mentioned factors.

The system may comprise sensors to monitor cardiovascular related information such as heart rate or blood pressure. Increased heart rate, blood pressure, or any other changes in a cardiovascular condition may indicate a heightened emotional state or stress level. A baseline reading may be taken of a driver 204 in a calm state and the changes that take place may be stored in data store 212 or sent to a central server via network 220.

Continuing with the embodiment depicted in FIG. 2, the system may comprise sensors, such as camera 208, that record facial expressions. Facial expressions may be processed using facial recognition software to determine the driver's 204 mood, emotional state, or stress level. Humans are typically very expressive and facial recognition software may be used to detect patterns related to how humans express themselves. The system may be loaded with default settings for recognizing the stress level of driver 204 and the system may update as new expressions are recorded. In this way, the system may be more personalized to the driver 204 of the vehicle 202 and may have profiles based on which person is driving the vehicle in the instance that multiple people drive the vehicle 202.

Embodiments of the system may also include the microphone 216, or any other sound measuring or recording sensors, and audio analysis equipment for measuring and detecting stress in the voice of the driver 204. A quick reaction by the driver 204 may be relayed through speech. The driver 204 may also indicate increasing levels of stress in the frequency and amplitude of voice. Analysis of the audio may be performed by the processor 210 or sent over the network 220 to be processed by a central server to provide a comparison of recorded audio with a baseline of audio. The system may also compare the recorded audio with audio recorded shortly before the recorded audio to monitor abrupt changes. For example, audio from the driver 204 may be captured and through analysis it is determined that the audio amplitude is higher than normal levels. When compared to other measured driver 204 conditions it appears that some are elevated and others are not. For example, a heightened emotional state may be detected without being a high level of stress; e.g., it may be determined that the driver 204 is singing and that no action should be taken. Alternatively, it may be that an increased level of stress is detected and that the vehicle 202 is stopped in traffic. A new driving route that corresponds to decreased levels of stress may be calculated and presented to the driver. In this example, the vehicle 202 may be provided a driving route based on the stress level of the driver 204. Driving routes may also be provided based on the stress levels of other drivers in the affective traffic environment.

The affective traffic environment may be the area related to the location, destination, and driving routes that may be presented to the driver 204 of the vehicle 202. The affective traffic environment may include all man-made and natural structures such as buildings, bridges, sidewalks, crosswalks, rivers, streams, lakes, trees, or any other man-made or natural objects that may affect the driving routes. The affective traffic environment may also include any information that may affect the driving routes that may be accessed from online sites or databases such as, traffic flow rate, traffic density, rain, snow, wind, construction site locations, road maintenance, road condition, or any other information that may be recorded or tracked and may affect any area that the vehicle 202 may come in contact with within a prescribed area relative to the vehicle 202 location and destination, and any possible driving routes.

Continuing with the exemplary embodiment of the invention depicted in FIG. 2, the respiratory rate may be detected using respiratory sensors as depicted as general sensor 218. The respiratory rate may be detected using visual information as recorded through the camera 208, pressure sensors in the seat and on the steering wheel (not shown), photoplethysmography sensors in or on the steering wheel, or any sensors or combination of sensors that may be useful in determining respiratory rate information. A heightened respiratory rate may be an indication of heightened stress levels and may be compared to a baseline respiratory rate and combined with other factors to determine a stress level of the driver 204.

The system of the embodiment of FIG. 2 may also analyze pupil dilation as one factor leading to a stress level determination. The pupil may dilate, indicating high stress levels. Pupil dilation may be an indicator of the brain thinking of a solution to a problem. This may be occurring in relation to the affective traffic environment the driver 204 is experiencing. This also may be an indicator of a heightened emotional state. Pupil dilation may be used as an indicator along with other factors associated with the stress level of the driver 204 to determine an accurate stress level to associate with the driver 204.

Muscle tension may be used as a factor for determining the stress level of the driver 204. Muscle tension may be determined by camera 208, pressure sensors, muscle contraction sensor that may be located in the steering wheel, seat, or on the driver 204 such as on the wrists, body, arms, legs, or head, and/or any other sensors that may be used to detect muscle tension.

In some embodiments, general sensor 218 may be configured to sense skin conductivity. Skin conductivity may be used to determine a stress level of the driver 204. A galvanometer may be used to detect galvanic skin response to stress. The system may measure and record the conductivity of the driver's 204 skin through galvanometers on the steering wheel, in the seat, or anywhere that the driver's skin may contact the vehicle 202. The system may store a baseline reading that may be updated when the driver 204 is determined by the system to be in a low-stress state. Measurements taken while driving may be compared to the baseline readings to determine a stress level or to be compiled with the other measured factors and a stress level may be determined from the combination of all factors.

In some embodiments, the movement of the driver 204 may be recorded and analyzed to determine the stress level of the driver 204. The driver 204 may have particular cues or gestures that signify a heightened stress level. The system may learn and store the gestures and automatically combine the data with data from other factors. The gestures may be hand, arm, shoulder, facial as described above, or any other gestures that may signify a change in stress level.

A profile for each driver if there are multiple drivers of the vehicle 202 may be stored. The condition of the driver 204 may be stored and adjusted over time. A baseline condition may be determined for each driver and adjusted or updated as more information is gathered. When the driver 204 turns the system on, the system may take an initial scan to determine the condition or stress level of the driver 204 as compared to the baseline reading of the driver 204. A determination of stress level may then be made based on the driver's 204 stored preferences and a history of the driver's 204 stress levels. The driver 204 may enter a destination and a route to the destination may be determined. The driver may have indicated that low stress should always be the best route, or a balance between stress and quickness may be entered into the system or determined based on the recorded history of the driver 204. The system may gather data from other vehicle and drivers in the area and determine an affective traffic environment based on the vehicle 202 location, destination, traffic conditions, and information from other vehicles.

Baseline measurements for all factors such as data collected from sensor measurements and/or stress levels may be determined for comparison against live measurements. The baseline information may be updated at any time. For example, the baseline information may be recorded and stored during low stress level times. It may be determined that all factors indicate low or no stress and the system may store the data as baseline data. Alternatively, the information may be tracked over time and averaged for baseline data. For example, the factors may be tracked during periods of time when the stress level is determined to be below a specified threshold. The data stored during this time may be used in any way, for example as averaged, to set baseline values. Baseline values may be set for each individual factor as described above or may be set as a combination of factors.

In some embodiments, the information gathered in vehicle 202 may be sent to and processed in a central server. Information may be gathered from any vehicle in wireless range of the central server. The information gathered might be data from the sensors depicted in the embodiment represented in FIG. 2, traffic, GPS information or any other information related to the affective traffic environment. The information may be received from any vehicle that transmits information and may be from vehicles that do not contain the system presented herein but only send location information. The information may also be gathered from a central database that stores and processes traffic information such as, traffic flow, construction areas, or any other information related to the traffic of an area that may be in range of the central server or vehicle 202. The information gathered can be regarded as factors that may relate to the driver's 204 stress level and may be combined and used to generate a stress map displaying levels of stress detected by drivers in different locations associated with an area evaluated by the central server. In some embodiments, multiple servers may be in communication to cover a larger area or in areas of high volume. In some embodiments, each vehicle may have a server in communication with other vehicles and the information may be processed at each vehicle.

Neural network, machine learning, fuzzy logic, statistical algorithms, or any other algorithm may use information from all vehicles, or individual vehicles, to create a network of vehicles working together. In some embodiments, each vehicle algorithm is weighted toward the emotion of the occupant of that vehicle. All vehicles could be weighted equally or some may be given more importance such as emergency vehicles. Some may be given more importance or weighted differently based on an occupant's tendencies such as if one occupant is more likely to get stressed than another occupant or if one occupant has a history of mental illness, anger management issues, or road rage. The driving routes may be based on the location of vehicles with stressed drivers and may work together to alter the diving routes to minimize the stress of individual drivers or all drivers simultaneously. The driving routes may be based on stress zones that define an area around the stressed drivers that will be discussed in greater detail below.

Figure 3:
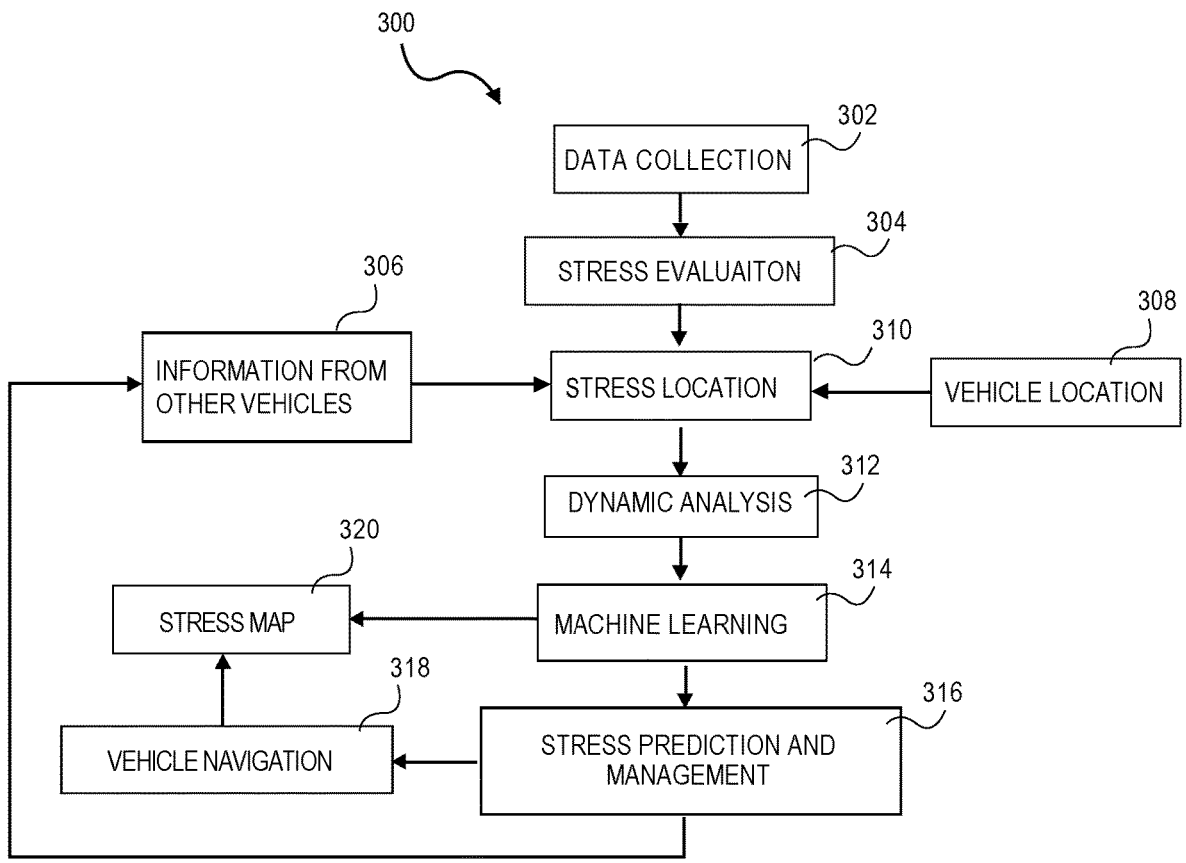
FIG. 3 depicts a flow chart representing exemplary method for embodiments of the invention.

Turning now to FIG. 3, an exemplary system flow chart representing embodiments of the invention is presented. The system may perform a first step 302, collecting stress data. The stress data collected may comprise individual factors detected from the driver 204 of the vehicle 202 presented in FIG. 2. The data may be collected and stored on the vehicle 202 data store 212 or uploaded to the central server via the network 220 as described above. Each vehicle connected to the system may have an associated number or profile for the vehicle and for individual drivers of each vehicle.

The system may then move on to a second step 304, evaluation of the stress data or factors. The stress data may be collected from the sensors as described in the exemplary embodiment depicted in FIG. 2. The measurements may be examined individually or as a combination of multiple measurements, or factors related to stress. A more accurate classification of stress level may be determined when all factors are considered. A stress level may be determined for each factor then combined or the measurements may be compiled and then a stress level determined from the combination of factors. For example, the driver's 204 pupils may dilate. While no other factors have measured above baseline readings it may be determined that the driver is not in a heightened stress state. Alternatively, the pupils dilate, a hand gesture that is flagged as a stress indicator occurs, the driver's 204 muscles become tense, and the skin becomes more conductive. The stress data, in combination, may provide enough indication that the driver is in a heightened stress state that a stress level is assigned to the driver 204 and the stress data may be stored under the stress level to provide the machine leaning algorithm more data to update the profile.

The sequence of individual factors may also be considered when determining a stress level. For example, there may be a slight delay in galvanic skin response and pupil dilation. A hand gesture may be sensed but at the same time the pupil data and the skin conductivity data is normal. Then just after the gesture the other pupils dilate and the skin becomes more conductive. The sequence of events may be an indicator of a heightened stress level. Data may be stored for short periods when an event takes place to compare to other factors in a sequential way. Using all factors in combination and the sequence of factors may lead to determining more accurate stress levels.

Moving now to step 306. Information from other vehicles may be combined with the information supplied by the vehicle 202 to construct a map of high and low stress areas, or stress zones. The information provided by all vehicles may include the stress data as described above and information related to the vehicle or traffic. Information related to the vehicle may be any operational information such as speed, acceleration, temperature, or any other relevant data such as location and heading provided by, for example, GPS. The vehicle location 308 may be the location of all vehicles, and used in conjunction with the other vehicle information to determine a route for the vehicle 204. The information may be updated continuously or periodically but may update often enough to track the traffic and stress changes in near real time.

Moving to step 310, the combination of all vehicle information may be used to define locations of high and low stress levels that may be referred to as stress zones. Stress zones may be areas where drivers have heightened stress levels. The stress zones may be determined from the stress data of drivers and the location of the stressed drivers. The stress zones may have levels such as low, medium, and high, or may be rated on a continuous scale such as 0-100%, 0% being no stress and 100% being the highest level of stress. The stress levels may be rated as a combination. For example, the stress level of an area may be determined to be 50%. The stress zone level may be presented as 50%, medium, and may also be presented with a color such as green for low, yellow for medium, and red for high. Stress levels are discussed in more detail below.

Moving to step 312, dynamic analysis is performed. The system may collect the data from the vehicles continuously or in bursts of short increments allowing the system to track and adjust the stress zones, locations of the vehicles, and stress levels of the drivers of the vehicles over time. This allows the system to analyze the traffic environment both spatially and temporally. This may be helpful in determining an ideal driving route by predicting when and where the driver may encounter a stress zone as they both move through the stress map. For example, as the driver 202 may navigate a driving route that has been provided by the system an accident may occur, or a stress zone may move into the driving route. The system may automatically provide an alternate driving route around the accident or stress zone. This provides the driver 204 an option to avoid stressful situations that may arise in real time.

Moving to step 314, the system may incorporate machine learning, fuzzy logic, neural networks, statistical algorithms or any other mathematical concept, theory, algorithm, or functionality to provide the necessary data processing required to take the stress data and learn the profiles, output the dynamic stress map, stress zones, driving routes, autonomous vehicle control, and any other output that may be useful for navigating a vehicle through the affective traffic environment.

Moving now to step 316, the system may predict the stress level of the driver of the vehicle navigating the stress map. The predicted stress level may be determined from the stress level of the stress zones, a history of the stress levels, and how the stress levels of past stress zones affected the driver. The predicted stress level may be used to predict driving routes for the driver. A stored history of the stress zones and the drivers within the stress zones may also be stored. This information may be used to predict how the stress zones, and vehicles within the stress zones may move to better predict a driving route to avoid stressful areas.

Moving to step 318, a driving route, or vehicle navigation plan, may be provided to the driver. The driving route may be based on the vehicle 202 location, destination, traffic data, and the driver stress and location data from other vehicles. The driving route may be a route that provides the least amount of stress as predicted by step 316. The driving route may be weighted and may consider time of travel or number of stops. The driving route may be displayed on the stress map in step 320. Driving route options may be suggested to the driver and the driver may choose the driving route, the driving route may be selected by the system from a set of possible routes, or the system may find a single best route based on optimizing weighted stress and vehicle data. The system may also consider driver preferences and settings. For example, the driver 204 may input a preference to have the system determine the best route based on a 50/50 weighting of stress and speed. Alternatively, the driver 204 may be in a hurry and have saved settings. The driver 204 may choose, for example, setting four which is 100% weighted to speed and does not consider stress levels, or vice versa. The driver 204 may also have the system set to make all decisions such that the driver 204 has as little stress as possible. Any options for levels of input by the driver 204 may be used from no input to 100% driver choice. Any weights may be updated dynamically based on the driver's 204 inputs and measured stress levels.

Moving now to step 320 stress map generation is performed. The stress map may be generated from the central server or the on-board processor 212. The stress map may present a GPS navigation map to the driver 204 and provide stress zones where other vehicles indicate high stress drivers. The stress map may also display driving routes to the driver 204 that avoid the stress zones. The stress map is described in more detail below.

Turning now to FIGS. 4A-C, depicting an exemplary stress map 400 in some embodiments of the invention. The stress map 400 may display an affective traffic environment associated with the current location of vehicle 402, denoted by point A, and a destination for vehicle 402, denoted by point B. In some embodiments, vehicle 402 may be vehicle 204. For example, the stress map 400 may display an area with a radius of 100, 500, or 100 feet; one, two, five, or one hundred miles; or any distance from the vehicle 402 less than, between, or greater than the distances provided. The stress map 400 area may be any shape and display geographical and man-made structures such as buildings 404 as well as other vehicles 406 and any traffic information that may be relevant such as construction, traffic speeds, estimated time to destinations, GPS information, and congestion. The stress map 400 may also be provided over satellite imagery.

In some embodiments, a stress zone 408 may be depicted on the stress map 400 indicating to the drivers where high stress areas are located. The stress zone 408 depicted in the exemplary embodiment in FIG. 4A may be high-level stress zone 408 and created because it has been determined that the driver of the center vehicle 410 is has a high stress level. The stress zone 408 levels may be determined from the stress level of the drivers within a stress zone 408, by the number of vehicles 406 in a stress zone 408, and by the number and level of stressed drivers in a stress zone 408. The stress levels of the drivers may be determined from the factors and methods as described above.

As the vehicles 406 move, the stress zone 408 may change shape and size. The stress zone 408, as depicted is a circle, but may be any shape and size, including any shape and size of the roads that the vehicles 406 may be on. The stress zone 408 levels may be indicated by different colors or numbers and routes both through and around the stress zone 408 may be provided to the driver by the system.

Continuing with the embodiment depicted in FIG. 4A, the stress zone 408 may project a distance away from a stressed driver or drivers. For example, the stress zone 408 may be any region within 500 feet, 100 feet, or one half mile of a stressed driver. As two or more drivers stress zone overlap that region may have a higher stress level and may be indicated as so with a different color, symbol, or number. Though in this embodiment the stress zone 408 is circular it should be noted that the stress zone 408 may be any shape and the shape of the stress zone 408 may conform to the roadways on the stress map 400.

The stress zone 408 may update continuously or periodically as stated above regarding the update of the stress map 400. Upon updating, the system may supply alternate routes. The system updates dynamically and the system may make in route changes to a route based on the dynamically changing environment. For example, an original driving route 412 as depicted in FIG. 4A may be presented to the driver, however, during the course of the vehicle 402 following the original driving route 412 the stress zone 408 may appear. Upon detecting the stress zone 408 the system may present the driver with an alternative driving route 414 to provide the driver with the option of taking a less stressful route. In the event that the vehicle 402 is autonomous, the vehicle 402 may make the adjustment and take the alternate driving route 414 or continue on the original driving route 412 automatically based on the settings of the autonomous-driving vehicle 402.

Continuing with the exemplary embodiment depicted in FIGS. 4A-C, the stress map 400 is presented representing a dynamic change in the stress map 400 over time. The stress zone 408 may move and the movement of the stress zone 408 may be tracked by the system. Based on the stress zone 408 past movement and traffic information the system may make a prediction as to where the stress zone 408 will be when the vehicle 402 reaches the affected area. For example, the system may predict that the stress zone 408 may move to the south as depicted in FIGS. 4B and 4C. It may be predicted that it will take 15 minutes to reach the point at which the vehicle 402 will come into the moving stress zone 408. The best driving route around the high stress zone 408 as determined from the description above may be the alternate driving route 414 and may be presented to the driver of the vehicle 408 or automatically uploaded into the vehicle's 408 autonomous driving system. The vehicle 402 may take the alternate driving route 414 as the stress zone 408 moves south as depicted in FIGS. 4B and 4C, and the vehicle 402 reaches the destination point B while avoiding the stress zone 408.

FIG. 5 depicts an exemplary flow chart 500 representing an embodiment of the invention. In a first step 502, a driver may start a vehicle. In some embodiments, the driver may be driver 204 and the vehicle may be vehicle 202. Upon ignition, the system may automatically start. The system may be connected to the vehicle power or have a separate power source. The system may be started manually or automatically. The driver may relay destination information to the system either by push button, touch screen, or by voice. The system may provide a map and driving route to the driver. Any portion of the driving route may also be provided to the driver audibly such that the driver does not have to look at the display.

Moving to step 504, stress data may be measured. Sensors, such as galvanometers, pressure, cardiographs, cameras, microphones, or any other sensors that may detect any state of the driver that may be a factor in determining a stress level of the driver as described above.

In step 506, a stress level of the driver may be determined from the stress data. The stress level may be determined in step 508 by comparing the stress data with baseline stress data and employing machine learning, fuzzy logic, neural networks, or any other statistical algorithm, mathematical concept, theory, algorithm, or functionality to provide the necessary data processing required to determine the stress level of the driver.

In step 510 the vehicle location may also be measured. The vehicle location may be measured by GPS, satellite triangulation, cellular signal, close-proximity signaling methods, or any other method that determine the location of a vehicle or electronic transmitting or receiving device. Information indicative of the traffic near the vehicle or along the driving route to the destination may also be measured such as location of other vehicles, traffic flow rate, construction area locations, emergency information, or any other traffic related information may be accessed. Weather related information such as weather alerts, snow, rain, ice, wind, or any other weather related information that may affect traffic may be accessed.

In step 512 the vehicle information, including stress data and vehicle location data, may be sent to a central server. The vehicle information may be sent over satellite communication, close-proximity wireless communication between vehicles, cellular, or any other method of wired or wireless communication. The information may be sent in any time interval including at the highest sensor update rate or all sensor data may be compiled and sent at a lower update rate. The stress data and stress level may be sent periodically or aperiodically at any time.

In step 514, the system may calculate the stress map. The central server may use the vehicle information from the vehicle and any other vehicles in an affective area as defined by the system, the location and destination of the vehicle, and generate the stress map as described above.

In step 516, the system may calculate or predict a future stress map. Based on the history of the stress data, the system may calculate probabilistic movements of the stress map and determine where the stress zones may be in the future. The movement of the stress zones may be calculated using data from online traffic databases, weather models, traffic flow, location of any vehicles in or out of the affective traffic area, stress levels of any driver in or out of the affective traffic area, and historical data of any of the above-mentioned factors.

In step 518 the system may calculate the driving route, which may be a most stress-free route. The most stress-free driving route may be determined based on the location of the stress zones on the stress map and the future location of the stress zones. The most stress-free route may be combined with user preferences or the most stress-free route may be based on a learned history of the particular driver such that a customized stress-free driving route is calculated. The most stress-free driving route may be based on the other vehicles in the affective traffic environment or all vehicles in the affective traffic environment. The driving route may also be based on vehicles that may be out of the affective traffic environment but are within range of the online traffic information, in communication with the central server, or in communication with a server that is in communication with the central server.

In step 520, the driving route is presented to the driver. The driving route may be displayed to the driver electronically on a map within the vehicle. The device presenting the map may be in communication with the central server and may provide audible instructions or information to the driver to allow the driver to remain attentive to the roadway.

In some embodiments, the vehicle may be autonomous. The driving route may be used by the vehicle to navigate without the aid of the driver. The occupant of the vehicle may be calm since the occupant does not have the stress of driving. The occupant may also not have to make decisions. However, in the autonomous vehicle, the occupant may have the ability to decide the driving route the vehicle takes based on the settings of the system. The vehicle may not have an occupant and may be a package delivery vehicle may and the route provided may be the safest route based on the stress level of drivers of other vehicles.

In some embodiments, steps of the flow chart 500 may be rearranged or omitted. Additionally, any portion of any step may be added to a different step or omitted. For example, step 502 presents a map to the driver and a possible driving route. The map and driving route may not be presented until step 518. In another example, the stress level calculation in step 506 may be performed at the central server after the vehicle information has been sent to the central server. Additionally, the vehicle may be in direct communication with other vehicles and all calculations may be performed on the vehicle without the central server.

Many different arrangements of the various components depicted, as well as components not shown, are possible without departing from the scope of the claims below. Embodiments of the invention have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims. Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A system for generating a map of an affective traffic environment based at least in part on a first location and a destination of a first vehicle, comprising:
   a first sensor configured to collect a first set of data associated with a first driver of the first vehicle;
   a second sensor configured to collect a second set of data associated with a second driver of a second vehicle distinct from the first driver;
   a processor; and
   one or more non-transitory computer storage media storing:
      a history of the first set of data;
      a first driver profile based at least in part on the first set of data;
      a second driver profile based at least in part on the second set of data;
      the destination and the first location of the first vehicle; and
      computer-executable instructions that, when executed by the processor, perform a method of generating the map of the affective traffic environment based at least in part on the destination and the first location of the first vehicle, comprising:
calculating a first stress level from the first driver profile;
calculating a second stress level from the second driver profile;
calculating a stress zone based at least in part on the second stress level of the second driver and a second location of the second vehicle;
predicting a future stress level of the first driver of the first vehicle based at least in part on the history of the first set of data and the stress zone;
determining a modified stress zone including the future stress level of the first driver of the first vehicle;
causing the map to display the modified stress zone including the future stress level of the first driver;
calculating a driving route for the first vehicle based at least in part on the modified stress zoned; and
communicating with a second processor configured to display the map of the affective traffic environment to the first driver,
wherein the map includes the driving route and the modified stress zone.

2. The system of claim 1, wherein the first sensor is at least one of a galvanometer, a pressure sensor, a cardiovascular sensor, a camera, a microphone, a photoplethysmograph, and a thermometer.

3. The system of claim 1, wherein the second set of data is indicative of at least one of a measured heart rate, a facial expression, a voice, a breath rate, a pupil dilation response, muscle tension, skin conductivity, and movement.

4. The system of claim 1, wherein the modified stress zone is further based on the second stress level.

5. The system of claim 1, wherein the method further comprises:
storing a location history of the second location of the second vehicle; and
predicting a location of the stress zone based at least in part on the location history of the location of the second vehicle.

6. The system of claim 5, wherein the driving route is further based at least in part on a predicted location of the modified stress zone.

7. The system of claim 1, wherein the first stress level is based at least in part on a determined emotion of the first driver of the first vehicle.

8. The system of claim 1, wherein the map further displays man-made and natural objects.

9. The system of claim 1, wherein the first sensor is a camera configured to continuously capture imagery of the first driver of the first vehicle.

10. A method of generating a map of an affective traffic environment based at least in part on a destination and a first location of a first vehicle, comprising:
collecting via at least one sensor a first set of data associated with a first driver of the first vehicle;
storing a history of the first set of data;
collecting via at least one second sensor a second set of data associated with a second driver of a second vehicle distinct from the first driver;
determining a first stress level from the first set of data and a first driver profile;
determining a second stress level from the second set of data and a second driver profile;
generating the map of the affective traffic environment;
generating a stress zone based at least in part on the second stress level and a second location of the second vehicle;
predicting a future stress level of the first driver of the first vehicle based at least in part on the history of the first set of data and the stress zone;
determining a modified stress zone including the future stress level of the first driver of the first vehicle;
generating a recommended driving route for the first vehicle based at least in part on the modified stress zone and the future stress level of the first driver of the first vehicle; and
displaying the map of the affective traffic environment of the first vehicle, the modified stress zone including the future stress level of the first driver, and the recommended driving route to the first driver of the first vehicle.

11. The method of claim 10, wherein the stress zone is further determined from a location history of the second location of the second vehicle.

12. The method of claim 11, wherein the stress zone is further determined from information associated with other vehicles in the affective traffic environment.

13. The method of claim 10, wherein the first set of data and the second set of data is indicative of at least one of a measured heart rate, a facial expression, a voice, a breath rate, a pupil dilation response, muscle tension, skin conductivity, and movement.

14. The method of claim 10, further comprising:
determining a baseline stress level based at least in part on the history of the first set of data, wherein the recommended driving route is generated based in further part on a comparison of the first set of data and the history of the first set of data.

15. The method of claim 10, wherein data defining the recommended driving route is configured for the first vehicle to use for navigating the recommended driving route autonomously.

16. One or more non-transitory computer storage media storing computer-executable instructions that, when executed by a processor, perform a method of generating a map of an affective traffic environment based at least in part on a destination and a first location of a first vehicle, the method comprising:
sensing a first stress level of a first occupant of the first vehicle;
storing a history of a set of data associated with the first stress level in a data store;
generating the map of the affective traffic environment of the first vehicle based at least in part on the first location of the first vehicle;
displaying the map of the affective traffic environment to the first occupant of the first vehicle;
generating a stress zone based at least in part on data received from a second vehicle,
wherein the data received from the second vehicle is a second stress level of a second occupant of the second vehicle distinct from the first occupant of the first vehicle;
predicting a future stress level based at least in part on the history of the set of data and the stress zone;
determining a modified stress zone including the future stress level of the first occupant of the first vehicle;
displaying the map including the modified stress zone including the future stress level of the first occupant of the first vehicle; and recommending a driving route to the first occupant of the first vehicle via the map of the affective traffic environment, wherein the driving route is based at least in part on the first stress level of the first occupant of the first vehicle, the first location of the first vehicle, the destination of the first vehicle, the future stress level, the modified stress zone, and information associated with other traffic in the affective traffic environment.

17. The media of claim 16, wherein the information associated with the other traffic in the affective traffic environment is at least one of a second location, a speed, and an acceleration of at least one vehicle in the affective traffic environment.

18. The media of claim 16, wherein the method further comprises:

storing a stress history of the first stress level in the data store; and determining a baseline stress level based at least in part on the history of the first stress level stored, wherein the first stress level based at least in part on the baseline stress level.

19. The media of claim 16, wherein the set of data is a first set of data, wherein a second set of data is indicative of at least one of a measured heart rate, a facial expression, a voice, a breath rate, a pupil dilation response, muscle tension, skin conductivity, and movement.

20. The media of claim 16, wherein the method further comprises:

wherein the modified stress zone is further based at least in part on the information associated with the other traffic in the affective traffic environment, wherein the driving route is further based at least in part on the stress zone.

* * * * *